US012667360B2

(12) United States Patent
Rangwala

(10) Patent No.: US 12,667,360 B2
(45) Date of Patent: Jun. 30, 2026

(54) IMPLANT DELIVERY SYSTEM WITH MULTIPLE DETACHMENT MECHANISMS

(71) Applicant: MicroVention, Inc., Aliso Viejo, CA (US)

(72) Inventor: Hussain Rangwala, Villa Park, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 183 days.

(21) Appl. No.: 18/550,656

(22) PCT Filed: Mar. 18, 2022

(86) PCT No.: PCT/US2022/071230
§ 371 (c)(1),
(2) Date: Sep. 14, 2023

(87) PCT Pub. No.: WO2022/198240
PCT Pub. Date: Sep. 22, 2022

(65) Prior Publication Data
US 2024/0156459 A1 May 16, 2024

Related U.S. Application Data

(60) Provisional application No. 63/163,610, filed on Mar. 19, 2021.

(51) Int. Cl.
*A61B 17/12* (2006.01)
*A61B 17/00* (2006.01)

(52) U.S. Cl.
CPC .................. *A61B 17/12022* (2013.01); *A61B 2017/00022* (2013.01); *A61B 2017/12063* (2013.01); *A61B 2017/12068* (2013.01)

(58) Field of Classification Search
CPC .... A61B 17/12022; A61B 2017/00022; A61B 2017/12063; A61B 2017/12068;
(Continued)

(56) References Cited

U.S. PATENT DOCUMENTS

| | | |
|---|---|---|
| 7,740,637 B2 | 6/2010 | Gandhi et al. |
| 8,048,104 B2 | 11/2011 | Monstadt et al. |

(Continued)

FOREIGN PATENT DOCUMENTS

| | | |
|---|---|---|
| JP | 2012-523931 A | 10/2012 |
| JP | 2016-511065 A | 4/2016 |

(Continued)

OTHER PUBLICATIONS

WIPO, U.S. International Search Authority, International Search Report and Written Opinion mailed Jun. 10, 2022 in International Patent Application No. PCT/US2022/071230, 7 pages.
(Continued)

*Primary Examiner* — Richard G Louis
(74) *Attorney, Agent, or Firm* — Inskeep IP Group, Inc.

(57) ABSTRACT

A detachment system for an implant is described having a first detachment mechanism and a second detachment mechanism. Either or both of the first or second detachment system may be activated by the user depending on certain conditions or if one of the detachment mechanism fails.

19 Claims, 7 Drawing Sheets

(58) Field of Classification Search
     CPC .. A61B 2017/0003; A61B 2017/12054; A61B
                  2090/0807; A61B 17/1214; A61B
                             17/12113
     See application file for complete search history.

(56) References Cited

U.S. PATENT DOCUMENTS

| | | |
|---|---|---|
| 11,179,160 B2 | 11/2021 | Henkes et al. |
| 2005/0021023 A1 | 1/2005 | Guglielmi et al. |
| 2010/0268204 A1 | 10/2010 | Tieu et al. |
| 2013/0204290 A1 | 8/2013 | Clarke et al. |
| 2014/0277084 A1 | 9/2014 | Mirigian et al. |
| 2015/0289879 A1 | 10/2015 | Bowman |
| 2019/0231358 A1* | 8/2019 | Henkes ............ A61B 17/12172 |
| 2019/0365454 A1 | 12/2019 | Le et al. |
| 2022/0151635 A1* | 5/2022 | Kaufman .............. A61M 25/09 |

FOREIGN PATENT DOCUMENTS

| | | | |
|---|---|---|---|
| JP | 2019-520898 A | 7/2019 |
| WO | WO 2020/208349 A1 | 10/2020 |

OTHER PUBLICATIONS

European Patent Office, Extended European Search Report dated Dec. 2, 2024 in European Patent Application No. 22772392.1, 10 pages.
Japanese Patent Office, Office Action dated Jan. 20, 2026 with English translation in Japanese Patent Application No. 2023-556956, 11 pages.

* cited by examiner

IMPLANT DELIVERY SYSTEM WITH MULTIPLE DETACHMENT MECHANISMS

RELATED APPLICATIONS

This application is the U.S. National Phase of and claims priority to International Patent Application No. PCT/US2022/071230, International Filing Date Mar. 18, 2022, entitled Recoverable Electro Thermal Detachment Systems; which claims benefit of and priority to U.S. Provisional Application Ser. No. 63/163,610 filed Mar. 19, 2021 entitled *Recoverable Electro Thermal Detachment Systems*; both of which are incorporated herein by reference in their entireties.

BACKGROUND OF THE INVENTION

Delivery of implantable intravascular therapeutic devices to occlude or treat target sites throughout the body has become an increasingly popular and less invasive method of therapy. For example, implantable therapeutic devices have been used to control vascular bleeding, to occlude the blood supply to tumors, to occlude fallopian tubes, and to occlude vascular aneurysms (e.g., intracranial aneurysms). Some implantable occlusion devices include microcoils, expandable mesh devices, filters, stents, and similar devices that can be delivered to a target site and released by a delivery system. A detachment mechanism may be used to separate the treatment device or occlusion device from the delivery system at the target site.

SUMMARY OF THE INVENTION

An implant delivery system is described having a first detachment mechanism and a second detachment mechanism. Either the first detachment system or the second detachment system, or both, can be used to detach and release an implant.

In some examples, the first detachment mechanism is a primary detachment mechanism that is configured and intended to be activated first, while the second detachment mechanism is a secondary detachment mechanism that is intended to be activated second if the first detachment system fails to detach the implant. Alternatively, either the first detachment mechanism or the second detachment mechanism may be configured and intended to be used first. In another alternative, the first detachment mechanism and second detachment mechanism may be used simultaneously.

Put another way, in some examples the delivery system comprises a first detachment mechanism having a first attached configuration where the implant is releasably secured to the elongated pusher, and having a first detached configuration where the implant is released from the elongated pusher; and a second detachment mechanism having a second attached configuration where the implant is releasably secured to the elongated pusher, and having a second detached configuration where the implant is released from the elongated pusher.

In one example, any of the detachment mechanisms may comprise a thermal detachment mechanism, a mechanical detachment mechanism, an electrolytic detachment mechanism, or a thermal-mechanical detachment mechanism.

One of the detachment mechanisms may be configured to mechanically break a heat-severable tether. The primary detachment mechanism may be a thermal detachment mechanism to separate or break a heat-severable tether. The secondary detachment mechanism may be a mechanical detachment mechanism and may further include a fixed member (e.g., a disc) and a movable member (e.g., a disc) within a pusher of the detachment system. Both members may include a passage longitudinally positioned therethrough and which the heat-severable tether is positioned through. The pusher further comprises a fixed sharpened edge positioned between the two members. When the movable member is in a first position, its position and the position of the passages in both members are such that the heat-severable tether does not contact the sharpened edge and thereby remains unbroken. However, when the movable member is longitudinally or axially moved within the pusher (e.g., via a control wire), the angle or position of the heat-severable tether is changed such that it contacts the sharpened edge, thereby breaking tether. Hence, if the heater of the primary detachment mechanism fails to activate or upon activation fails to fully separate the implant from the delivery device, the heat-severable tether can be mechanically moved against the sharpened edge and broken via the secondary detachment mechanism.

Also described is a method for detaching an implant. The method comprises advancing an implant out of a catheter to a target delivery site or area where the occlusion device is attached to a distal end of a pusher via a detachment system. Next, a primary detachment mechanism is activated or actuated to attempt detachment and release of the implant. If the primary detachment system fails to cause complete detachment of the occlusion implant, a secondary detachment system is activated or actuated to cause detachment and fully release of the implant. Activating or actuating the primary detachment mechanism may further include activating or actuating a heater in proximity to a heat-severable tether. Activating or actuating the secondary detachment mechanism may further include mechanically positioning the heat-severable tether against a sharpened edge within the pusher so as to break the heat-severable tether.

Also described is a detachment system for a medical implant with a single, mechanical detachment mechanism. Specifically, the detachment system may solely include the "secondary" detachment mechanism described above, including the tether, fixed member, movable member, and sharpened edge. In another example, the detachment system may include two detachment mechanisms, both of which are mechanical (as described herein), both of which are thermal (as described herein), both of which are electrolytic (as described herein), or both of which are thermal-mechanical (as described herein).

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

3

Figure 4:
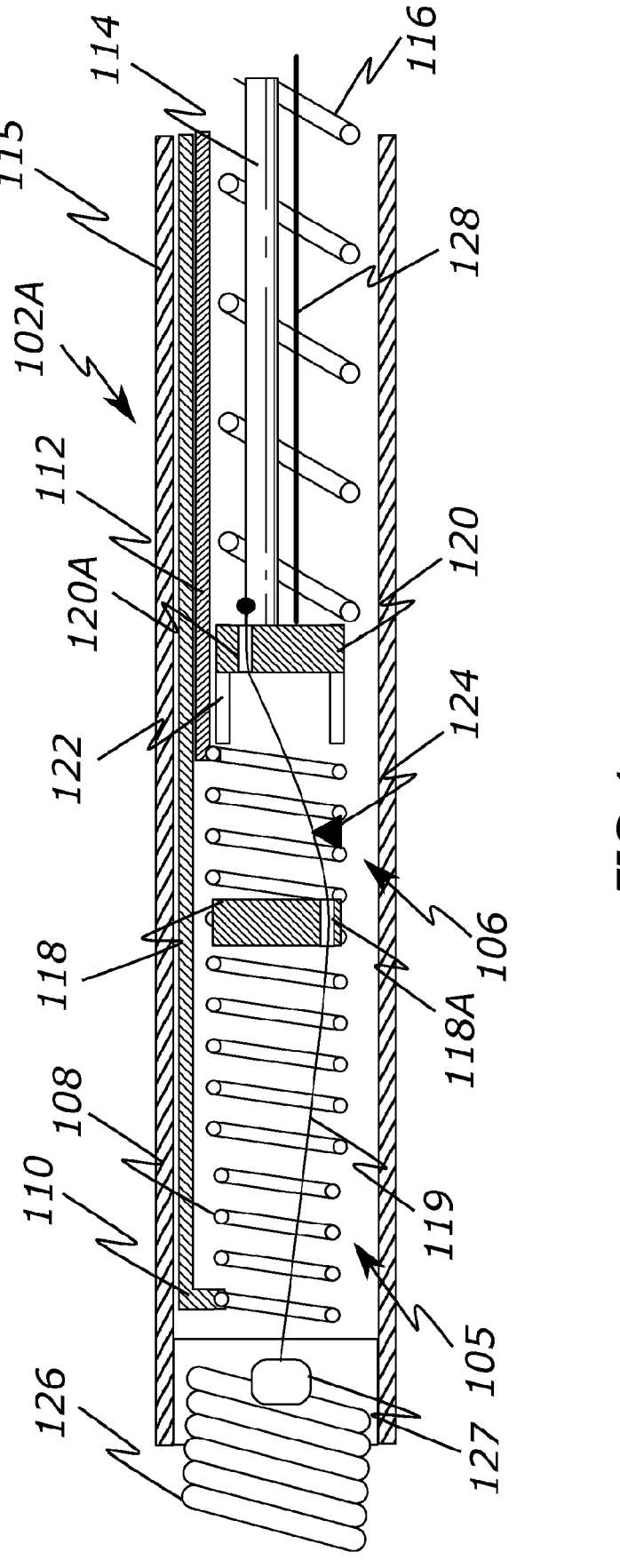

FIG. 4 illustrates a side view of a pusher with multiple implant detachment mechanisms in a second position according to the present invention.

Figure 5:
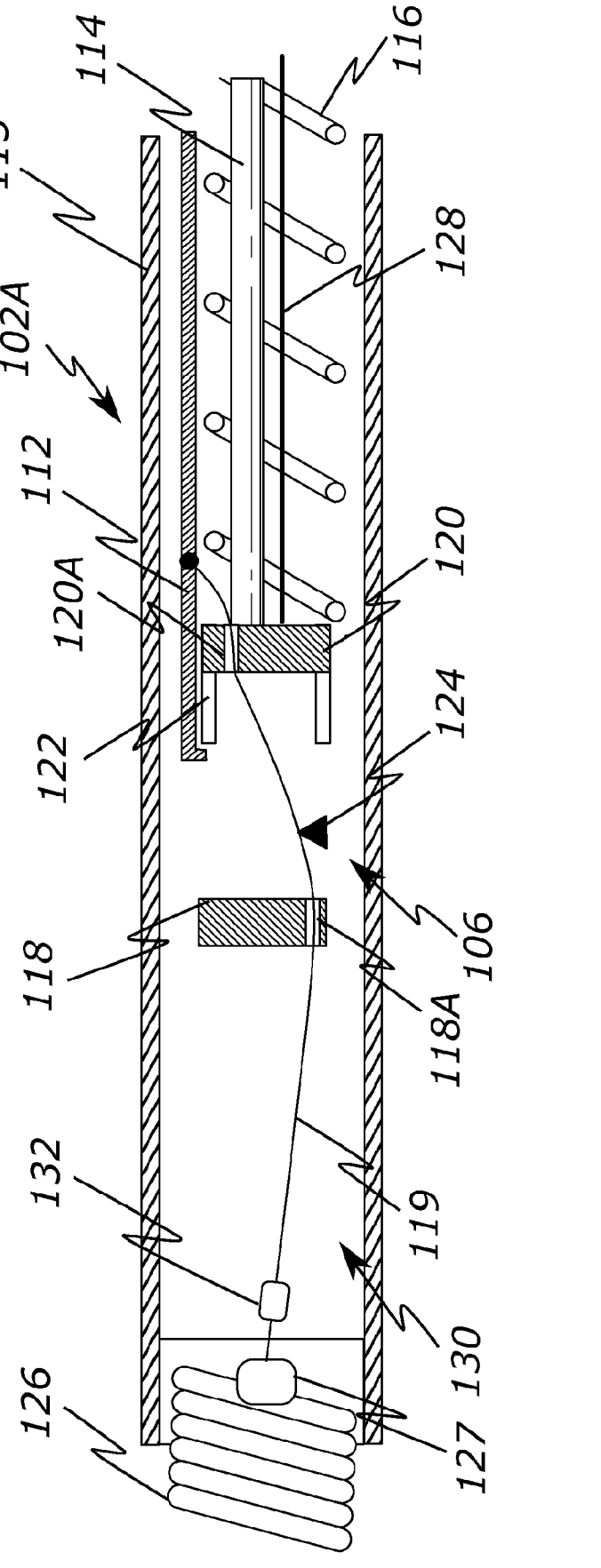

FIG. 5 illustrates a side view of a pusher with multiple implant detachment mechanisms according to the present invention.

Figure 6:
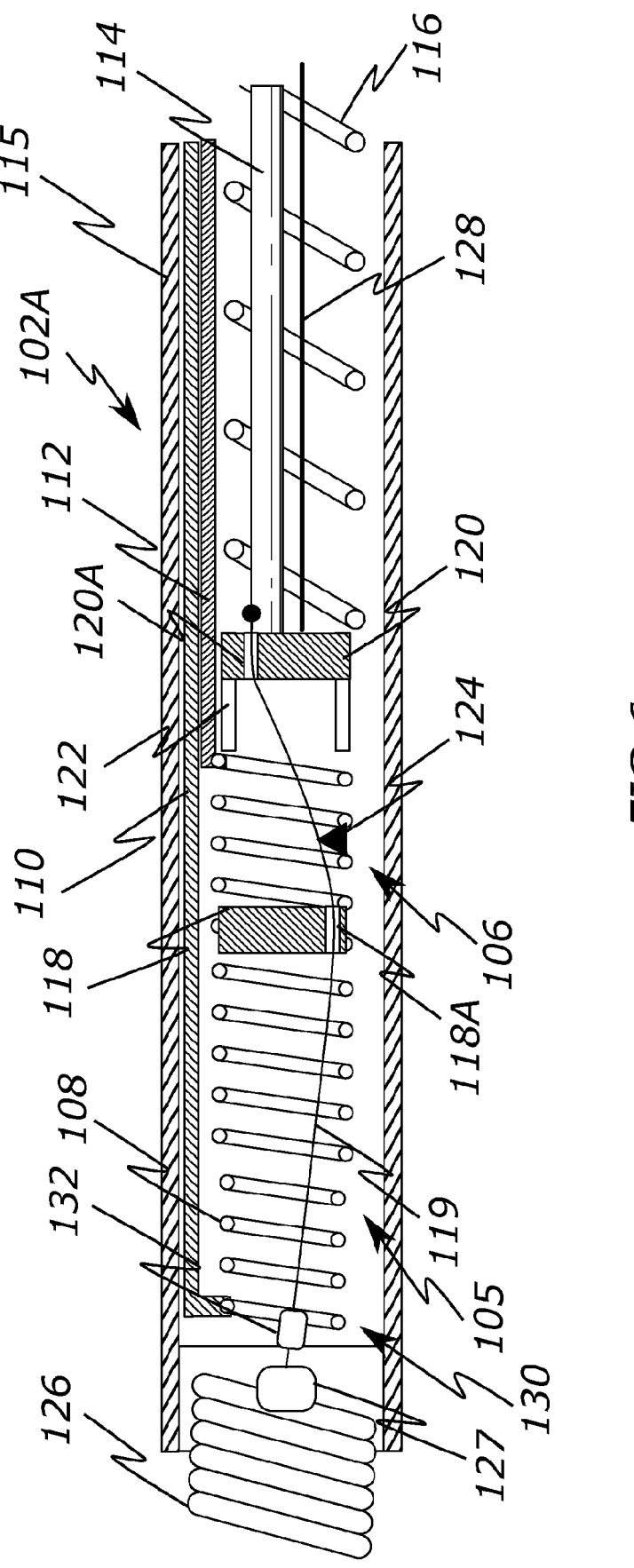

FIG. 6 illustrates a side view of a pusher with multiple implant detachment mechanisms according to the present invention.

Figure 7:
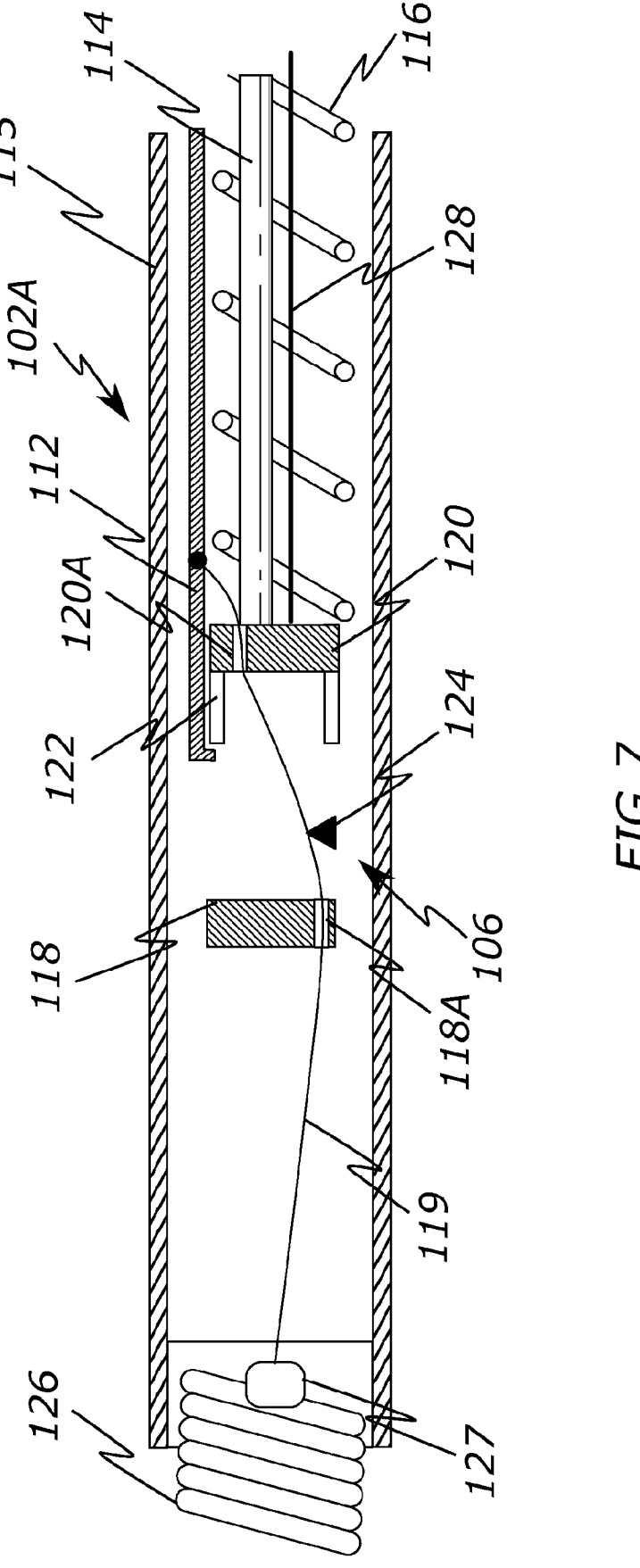

FIG. 7 illustrates a side view of a pusher with a single mechanical implant detachment mechanism according to the present invention.

DETAILED DESCRIPTION

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements. While different embodiments are described, features of each embodiment can be used interchangeably with other described embodiments. In other words, any of the features of each of the embodiments can be mixed and matched with each other, and embodiments should not necessarily be rigidly interpreted to only include the features shown or described.

The terms distal and proximal are used within this specification. Unless defined otherwise, distal and proximal are used in reference to the physician during a procedure. Hence, proximal tends to be closer to the physician while distal tends to be closer to a target location within a patient. However, this terminology is applicable whether the device is inside or outside of a patient.

This specification is generally directed to a detachment system for medical implants or devices. These implants specifically include microcoils, expandable occlusion devices (e.g., expandable mesh occlusion devices), filters, stents, and similar devices that can be delivered to a target site and released by a delivery system. However, use with other types of implants may also be possible.

These delivery systems may include an elongated pusher that is attached at its distal end to the occlusion device via a detachment mechanism. The detachment mechanism allows the physician to detach the occlusion device once it has been deployed into the patient at a desired location. In the case of aneurysm or other vascular malformation, the occlusion device restricts or blocks the flow of blood, eventually causing thrombosis and tissue growth tissue growth.

Several different types of detachment mechanisms may be used to retain and release occlusion devices. For example, mechanical detachment mechanisms, electrolytic detachment mechanisms, thermal detachment mechanisms, and thermal-mechanical detachment mechanisms can be used to deploy occlusion devices and other medical treatments. Some of these detachment mechanisms may include some drawbacks or possible points of detachment failure. If detachment fails to occur, procedural complications can result if there is not an alternative way to detach the implant (e.g., restraints on cross-sectional space and volume may prohibit the operator from inserting a second detachment device into the delivery system). In one example of a procedural complication, the operator (e.g., physician) may attempt to retract the implant into the delivery device, thereby dislodging the implant from the target site, increasing procedure time if the device is later redeployed, or resulting in a procedure failure if the device cannot be redeployed. Dislodging the implant may also result in damage to surrounding tissue. In another example, after a detachment failure, the operator may retract the implant into the delivery device and further retract the implant proximally to remove it from the delivery system, then later attempt to deploy and detach a second implant at the target site, thereby increasing overall procedure time.

A detachment system may utilize a mechanical grasping mechanism at the end of a pusher that engages a ball shape on the end of a microcoil. The grasping mechanism requires relatively exact sizing and tolerances, otherwise the ball shape may be allowed to slip out of the grasping mechanism and premature detachment may occur, or if oversized, the ball shape may not slip out of the grasping mechanism when detachment is attempted. Mechanical grasping mechanisms may rely on a pull wire that disengages the grasping mechanism from the ball. The pull wire may be difficult to actuate if it is tightly wedged against the ball shape or grasping mechanism, especially if the pusher is positioned in a curved region of a vessel.

A detachment system may utilize electrolytic detachment, which involves conducting electrical current through a patient's blood to an attachment wire of the microcoil, causing corrosion of the attachment wire. The attachment wire eventually severs and detaches the microcoil to deploy it to the target site. However, when an aneurysm site is filled with a relatively large mass of one or more microcoils, less blood is available at the site to conduct current and corrode the attachment wire, thereby making the electrolytic detachment of the microcoil difficult to achieve in some instances, and possibly resulting in detachment failure.

A thermal detachment mechanism may rely on a tether positioned in proximity to a heater. When activated, the heater melts or breaks the tether to release the microcoil. These thermal detachment systems also may rely on an electrical circuit within the delivery device (e.g., within a pusher) to supply electrical current to the heater. Typically, pushers have a relatively small diameter, a relatively long length, and are subject to significant bending as they are advanced through vessels of a patient to a target site. This may result in an interruption of (or disruption within) the electrical circuit or breakage of the electrical circuit during delivery, thereby preventing the heater from being activated by a physician.

An implant detachment system that can recover or otherwise detach its implant after a detachment system's primary detachment mechanism has failed or otherwise encountered difficulty detaching may avoid or minimize procedural complications and procedural failures, for example, by allowing the operator to fully detach the implant from the delivery system without dislodging the implant from the target site, without inserting additional components into the delivery system, and/or without retracting the implant into the delivery device.

A detachment system for an implant is described having a first detachment mechanism and a second detachment mechanism. Either the first detachment mechanism or the second detachment mechanism may be activated or actuated to cause the release of an attached implant. While two detachment mechanisms are primarily described in this specification, embodiments with three, four, or even more of the detachment mechanisms described herein are also possible.

There may be several reasons that two detachment mechanisms may be helpful to a physician during a delivery procedure. For example, one of the detachment mechanisms may fail to detach the implant after the physician has attempted to activate or actuate it. Hence, the other detachment mechanism may provide a backup detachment mechanism that may then release the implant. In another example, the location and/or vessel path to a target location may render one of the detachment mechanisms less desirable (e.g., providing unwanted heat to a sensitive area of a vessel or a particularly tortuous vessel path that may impinge on laterally moveable control wires).

The first and second detachment mechanisms can be any combinations of mechanical detachment mechanisms, electrolytic detachment mechanisms, thermal detachment mechanisms, and thermal-mechanical detachment mechanisms.

In one specific example, a detachment system may comprise a thermal detachment mechanism and a mechanical detachment mechanism. The thermal detachment mechanism may comprise a heater coil, heater loop, heater sleeve, or similar device configured to increase in temperature to break a tether connected to an implant. The mechanical detachment mechanism may comprise a sharp edge that is configured to selectively contact and cut or break the tether connected to the implant.

In another specific example, a detachment system may comprise a thermal detachment mechanism and an electrolytic detachment mechanism. The thermal detachment mechanism may comprise a heater coil, heater loop, heater sleeve, or similar device configured to increase in temperature to break a tether connected to an implant. The electrolytic detachment mechanism may include an electrolytically degradable member that is either the tether or connected to the tether, and which degrades when exposed to certain electrical current.

In another specific example, a detachment mechanism may comprise an electrolytic detachment mechanism and a mechanical detachment mechanism. The electrolytic detachment mechanism may include an electrolytically degradable member that is either the tether or connected to the tether, and which degrades when exposed to certain electrical current. The mechanical detachment mechanism may comprise a sharp edge that is configured to selectively contact and cut or break the tether connected to the implant.

In another specific example, a detachment system may comprise two independent thermal detachment mechanisms. The thermal detachment mechanisms may comprise a heater coil, heater loop, heater sleeve, or similar device configured to increase in temperature to break a tether connected to an implant.

In another specific example, a detachment mechanism may comprise two independent electrolytic detachment mechanisms. The electrolytic detachment mechanism may include an electrolytically degradable member that is either the tether or connected to the tether, and which degrades when exposed to certain electrical current.

In another specific example, a detachment mechanism may comprise two mechanical detachment mechanisms. The mechanical detachment mechanisms may comprise a sharp edge that is configured to selectively contact and cut or break the tether connected to the implant.

Any of the embodiments described in the specification may include a pusher that is moved axially or longitudinally within a tubular catheter or sheath. Generally, a pusher is an elongated member or body that is attached to an implant device and may include other components necessary for delivery and detachment of the implant. The pusher may or may not include a passage opening at its proximal and distal portions for a guidewire or other devices. In that respect, while the term pusher is used throughout this specification, the term may also encompass catheters or any elongated body that is sized and shaped for passage within a patient's vasculature.

The pusher may include two or more detachment mechanisms and is further moved via a proximal end of the pusher (e.g., via the pusher itself or a handle attached to the pusher).

Each of the attachment mechanisms may be considered to have an attached configuration and a detached configuration. In the attached configuration, the attachment mechanism is in a physical position, energized state (e.g., current delivery), temperature, or similar physical state that would otherwise prevent that attachment mechanism from releasing the implant attached to the pusher. For example, a thermal detachment system may not have current flowing through its components (e.g., a heater coil) and may be of an ambient temperature of the pusher. In another example, an electrolytic mechanism may be substantially non-degraded or non-corroded. In another example, a mechanical mechanism may have a shape or position of one or more of its parts that prevent release of the implant.

In the detached configuration, the attachment mechanism is in (or previously was in) a physical position, energized state (e.g., current delivery), temperature, or similar physical state that would, under normal operation, cause the implant to be released from the pusher. For example, a thermal detachment system may have (or previously had) current flowing through one or more of its components (e.g., a heater coil) and may be above an ambient temperature of the pusher (or previously was above an ambient temperature of the pusher). Thus, under normal conditions, after current flows through the components (e.g., heater coil) and the implant is released from the pusher, the attachment/detachment mechanism and components thereof may return to ambient temperature with the implant and pusher in the detached configuration. In another example, one or more components of an electrolytic mechanism (e.g., an electrolytic tether) may be partially or fully degraded or corroded. Under normal conditions, after the electrolytic mechanism degrades or corrodes the relevant component(s) (e.g., electrolytic tether) and the implant is released from the pusher, the attachment/detachment mechanism and components thereof may return to a neutral electrolytic state with the implant and pusher in the detached configuration. In another example, one or more components of a mechanical mechanism (e.g., sharp edge or blade) may change shape, position, or orientation to a detached configuration having a shape, position, or orientation of one or more of its parts that releases of the implant from the pusher.

While the attachment mechanism may be in a detached configuration and/or such a configuration may be initiated by a user (e.g., via a button or wire at a proximal portion of the pusher), failure of the detachment mechanism (or components related to it) may prevent the implant from being detached from the pusher. Hence, while under normal or intended circumstances the activation (or actuation or initiation) of one of the detachment mechanisms will result in the implant being detached from the pusher in the detached configuration, it is possible for the detachment mechanism to fail, and as a result, the implant would not be released or detached from the pusher despite activation (or actuation or initiation) of the detachment mechanism.

The detachment mechanisms of this specification discuss that the implant may be detached, released, and/or separated from the pusher. These terms may include complete detachment, release, and/or separation from the pusher. In the event of partial detachment, release, and/or separation (e.g., detachment failure or partial failure), the implant may still have a partial or residual connection or attachment to the pusher, and thus, a second detachment mechanism may be activated, actuated, or initiated to achieve full or complete detachment, release, and/or separation.

As previously discussed, one advantage of multiple detachment systems is that if one detachment system fails, a second can be actuated or activated. This failure to detach and subsequent actuation and activation may be performed solely by the user. For example, a user may use visual imaging (e.g., fluoroscopy) to determine if detachment has occurred and then manually actuate or activate a second detachment mechanism. This may allow the user to have control regarding whether use of the second detachment system is needed.

In another example, the detachment system may have a sensor that monitors and signals if the implant has detached from the pusher (e.g., by sensing inductance at a distal portion of the pusher). The detachment system may also, for example, have a mechanism that automatically activates the second detachment system after its sensor has determined that the implant has not detached after activation of the initially-activated first detachment system. In other words, the second detachment system can be an automatically actuated backup if the first detachment system fail to detach the implant. This may be advantageous in some situations if it is difficult to determine if detachment has occurred via imaging alone (e.g., fluoroscopy).

While a first and second detachment mechanism may be activated or actuated (or at least attempted to be activated or actuated) in a sequential manner, it may also be desirable for two detachment mechanisms to be activated or actuated simultaneously. For example, a single interface element (e.g., a button) may activate or actuate at least two detachment mechanisms at the same time. This may provide the user additional reassurance that implant detachment has occurred, especially in when imaging of the pusher and implant is difficult to view. In the case of detachment mechanisms that include a tether, it may be desirable to include mechanisms that break the tether close to or at the same location to prevent portions of the tether from separating from both the pusher and the implant.

Generally, a guidewire is initially advanced so that the distal end is located at a target location, then a catheter or sheath is advanced over the guide so that its distal end is located at the target location. The guidewire may be removed from the catheter, and the delivery system is advanced through the catheter so that its distal end is located near the target location.

A pusher of the delivery system may be distally advanced to push an implant (e.g., a microcoil) out of an outer sleeve or sheath. A first detachment mechanism within the pusher of the delivery system may be actuated or activated to attempt to detach the implant from the pusher, which preferably results in a complete or full detachment and separation of the implant from the pusher, but in some cases may only result in partial or incomplete detachment and separation, or possibly no detachment and no separation (e.g., if there is a break or interruption in the thermal or electrolytic detachment mechanism). In the event that activation of the first detachment mechanism results in anything less than a complete or full detachment and separation of the implant from the pusher, a second detachment system within the pusher of the delivery system may be actuated or activated to ultimately cause detachment and separation of the implant from the pusher and to deploy the implant at the target location of the patient.

FIGS. 1A, 1B, 2, 3, and 4 illustrate one example embodiment of a delivery system 100 that is configured to deliver and detach an implant. The presently described delivery system 100 includes two detachment mechanisms, though embodiments with more detachment systems are also possible.

While not required, the delivery system 100 may include a pusher 102, an outer sheath 103, and a handle 104. The pusher 102 is an elongated embodiment that is attached to an implant 126 at its distal end and attached to the handle 104 at its proximal end. The pusher 102 may be distally advanced relative to the tubular outer sheath 103 so as to push the implant 126 out of a distal end of the outer sheath 103 to a target location within a patient.

In an embodiment where electrical detachment mechanism is included, such as a heater, the handle 104 may include or be attached to a power supply (e.g., a battery) and include an actuation mechanism such as a button 104A to cause electrical current to pass into an electrical pathway of the pusher 102 to activate one of the detachment mechanisms.

In an embodiment where a mechanical detachment mechanism is included, a control wire 128 may pass through the handle 104 (if present) or out a distal end of the pusher 102. This allows a physician to push or pull the control wire 128 to actuate the mechanical detachment mechanism.

Generally, the pusher 102 includes a proximal portion 102B that extends much of its length, as well as a distal portion 102A. Both the distal portion 102A and the proximal portion 102B typically include an outer tubular layer 115 that may be comprised of a polymer or similar material. Typically, the proximal portion may also include other structural elements such as a structural coil 116 to provide some rigidity and pushability of the pusher 102.

In the present example, the distal portion 102A includes a first detachment mechanism 105 and a second detachment mechanism 106, either of which can be actuated or activated to release an implant 126 that is attached to the pusher 102.

The first detachment mechanism 105 is an electrically actuated or activated heater mechanism configured to break a tether 119 that is configured to secure the implant 126 to the pusher 102 and break the tether via application of heat. In that respect, a distal portion of the tether 119 is connected to the implant 126, such as via an adhesive 127. A proximal portion of the tether 119 may be connected to a proximal area of the pusher 102. This may be the structural coil 116, an internal core wire 114, components of the second detachment mechanism, or other proximal pusher components.

The tether 119 may be positioned through or near a heater coil 108 located in the distal portion 102A of the pusher 102 that is configured to selectively generate sufficient heat to cause breakage of the tether 119. In one example, the heater coil may have a helical shape that is connected to a first electrical wire 110 near its distal end and a second electrical wire 112 near its proximal end. The wires 110 and 112 extend and/or are in communication with a proximal end of the pusher 102 and may connect to a power source. For example, the handle 104 may include a battery power source that may selectively supply power to the wires 110 and 112 when the button 104A is actuated or activated, thereby creating heat in the heater coil 108. Optionally, the heater coil 108 may include a smaller diameter distal portion and a larger diameter proximal portion.

The second detachment mechanism 106 may provide an alternate mechanism for detachment of the implant 126. In the present example, both the first detachment mechanism 105 and the second detachment mechanism 106 are configured to break the tether 119, though this may not necessarily be required with other types of mechanism.

Specifically, the second detachment mechanism 106 is configured to move the tether 119 against a relatively sharp edge or blade 124 to cause breakage of the tether 119 and thereby release the implant 126. In one embodiment, moving the tether 119 against the blade edge 124 may generally include a mechanism having a control wire 128 that extends between the distal portion 102A and a proximal end of the pusher 102, such that when the user pulls the control wire 128, it causes breakage of the tether 119. Put another way, the sharp edge or blade 124 of the second detachment mechanism 106 is positioned near the tether 119 such that when in its detached configuration, the tether 119 is at least briefly positioned against the sharp edge or blade 124 to sever the tether 119.

Such a mechanical detachment mechanism may take many forms. For example, in FIGS. 3 and 4, the second detachment mechanism 106 is a mechanical arrangement configured to change a position or an angle of the tether 119 within the pusher 102 so that it pushes against the sharp edge/blade 124.

In one embodiment, the tether 119 may be positioned through two passages 118A and 120A within the pusher 102 to allow its position or angle within the pusher 102 to change. This angle or position change can be achieved by allowing one or both of the passages 118A and 120A to move relative to each other.

Figure 3:
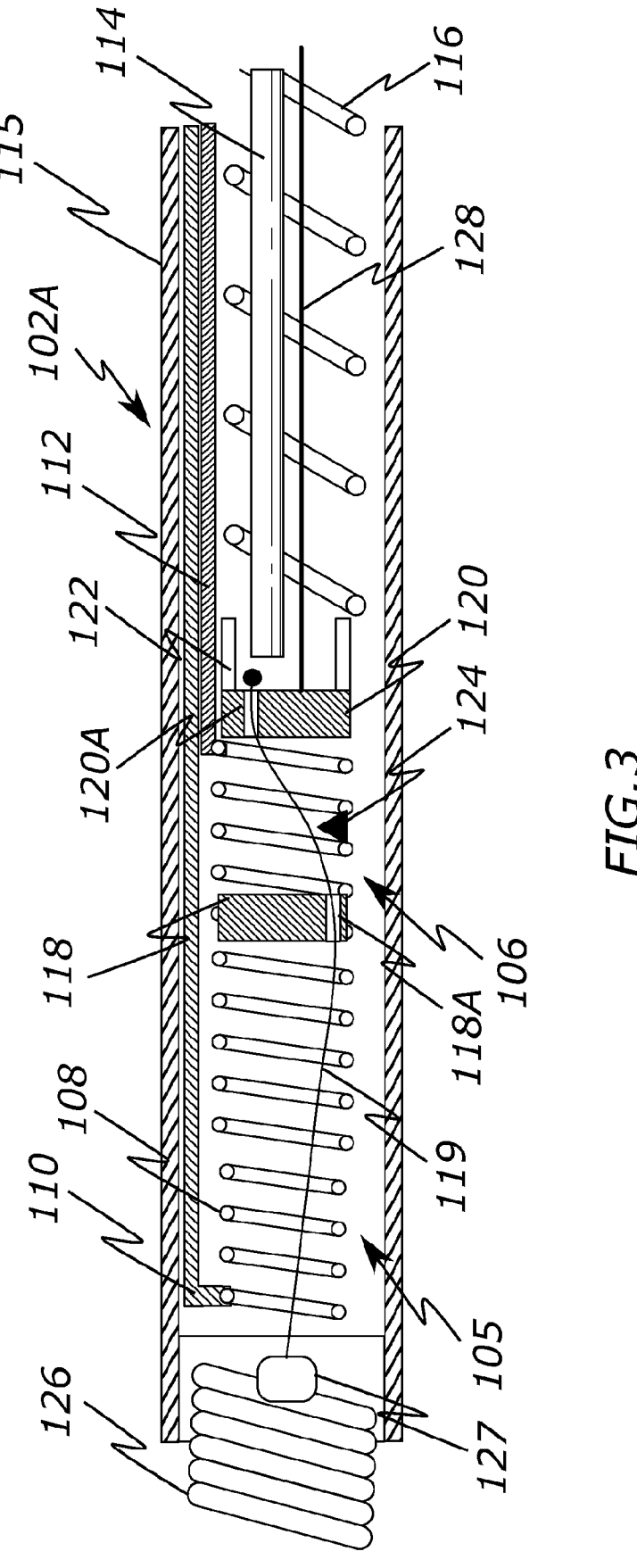
FIG. 3 illustrates a side view of a pusher with multiple implant detachment mechanisms in a first position according to the present invention.

In the present example of FIGS. 3 and 4, a distal end of the core wire 128 is connected to a movable member 120 that includes passage 120A. The movable member 120 is depicted as a generally circular disc-shaped body, but almost any shape and size member can be used, including a tube. The movable member 120 is configured to move longitudinally or axially with relation to the axis of the pusher 102 (i.e., it has at least a first longitudinal position and a second longitudinal position). This may be achieved by including a longitudinal groove or track 122 in which the movable member 120 is engaged with which allows the movable member 120 to move longitudinally only within the track 122. Optionally, a biasing element (e.g., a spring) may be included to bias the movable member 120 to a default "non-detached" position in which the implant 126 remains attached to the pusher 102.

The movable member 120 includes the previously discussed passage 120A through which the tether 119 is positioned into and/or through. Depending on the configuration, the passage 120A may be offset from the center or axis of the pusher 102 so that when the passage 120A and moveable member 120 are moved longitudinally, they create a change in the position or angle of the tether 119.

In a first position configured not to break the tether and detach the implant 126, seen in FIG. 3, the movable member 120 is positioned at a proximal position such that the tether 119 is not positioned or moved against the blade edge 124. When the control wire 128 is proximally retracted as seen in FIG. 4 (e.g., at a proximal end of the pusher 102), the movable member 120 is moved proximally and therefore changes the position and angle of the tether 119, moving it against the blade edge 124.

The angle of the tether 119 can be optionally increased to allow the tether 119 to have greater movement within the pusher 102 and against the blade edge 124. For example, a second, fixed member 118 with a tether passage 118A may be included distal of the movable member 120. The second fixed member 118 may be a circular disc or any other shape, such as a tube fixed to a side of the inside of the pusher. The passage 118A may be in a radial location different than, and optionally opposite of, the radial position of passage 120A so as to create a relatively large angle of the tether 119 within the pusher 102.

Figures 1A, 1B:
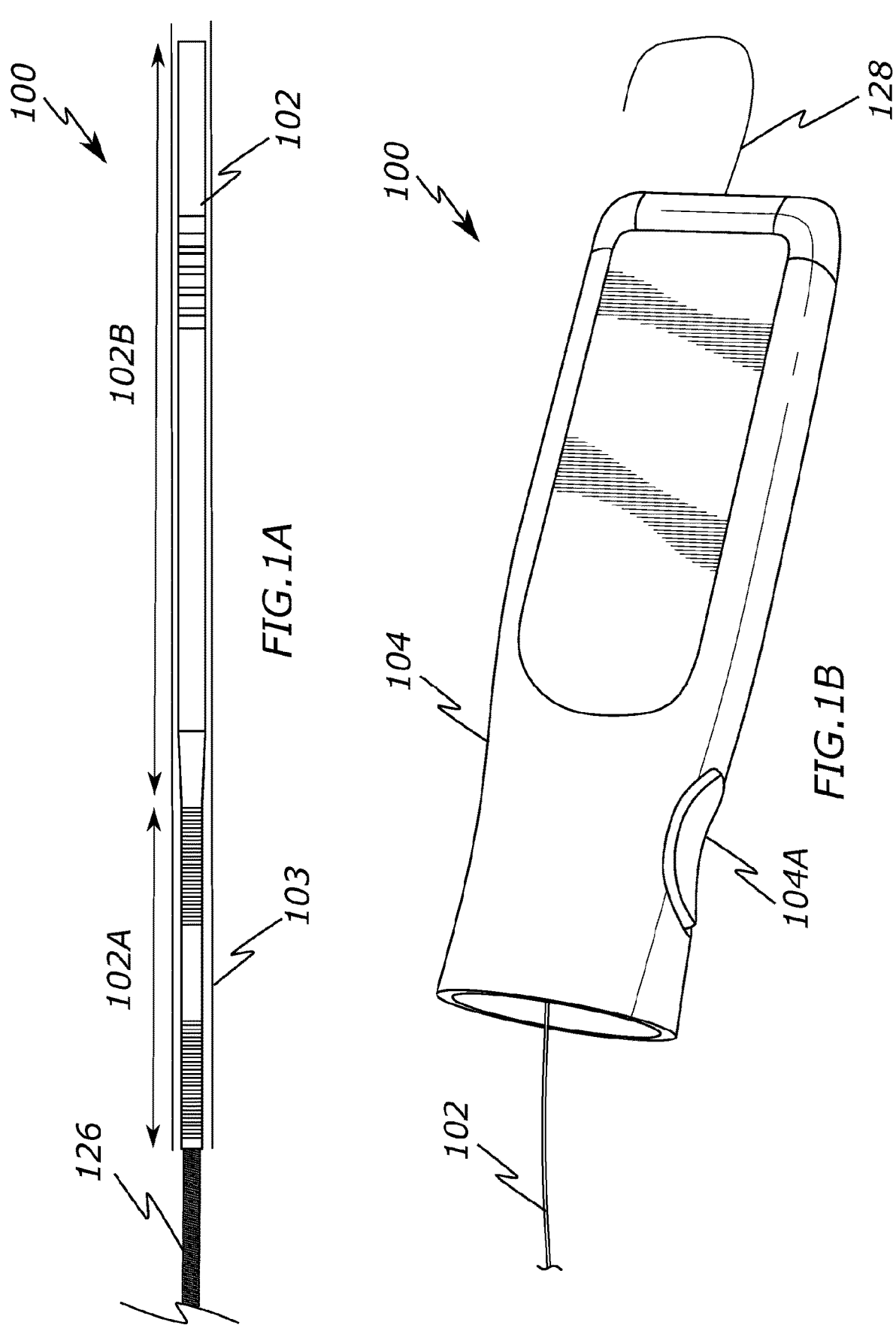
FIG. 1A illustrates a side view of a pusher and outer sheath of an implant delivery system according to the present invention.
FIG. 1B illustrates a side view of the pusher and a handle attached to the pusher according to the present invention.
Figure 2:
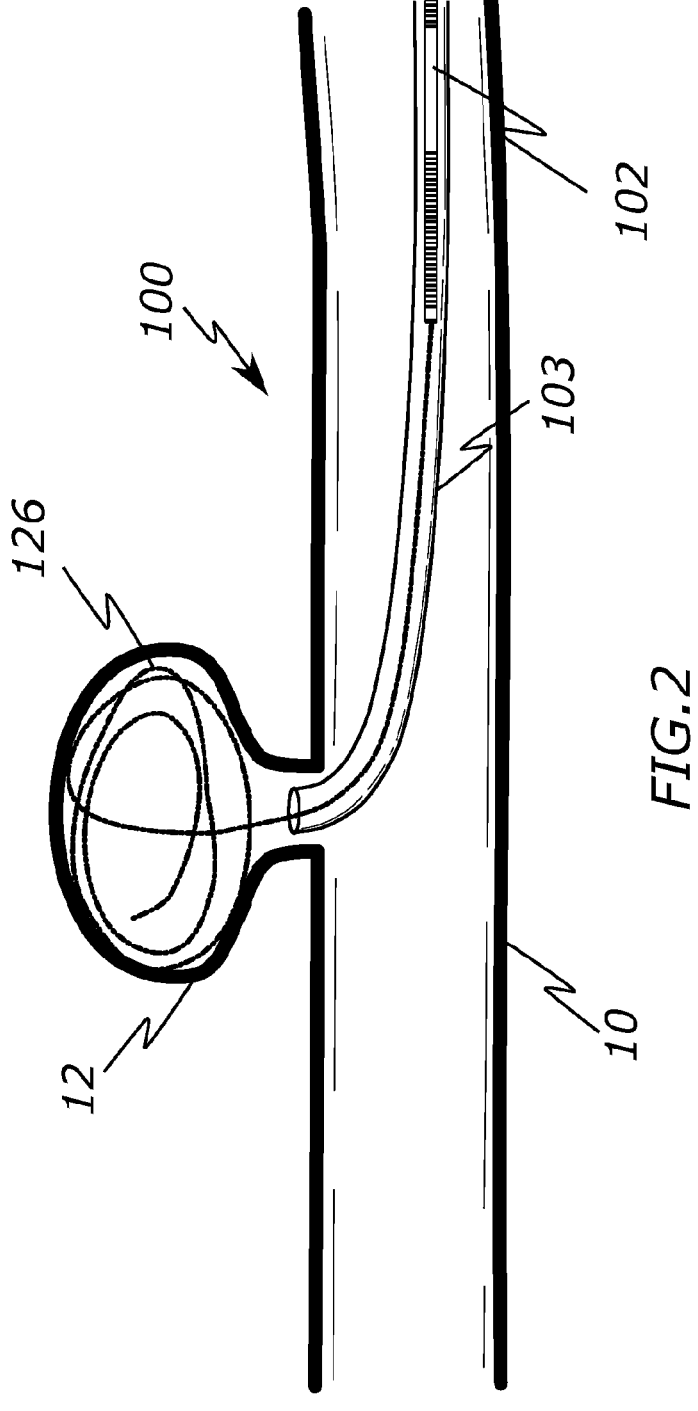
FIG. 2 illustrates a side view of the pusher advancing an implant to a target area according to the present invention.

In operation, a distal end of the delivery system 100 is advanced distally to or near a target location within a patient. For example, in FIG. 2, a distal portion of the delivery system 100 is advanced through a vessel 10 of a patient so that a distal opening of the outer sheath 103 is positioned near or within an aneurysm 12. The pusher 102 is distally advanced relative to the outer sheath 103 to push the implant 126 out of the sheath 103. In the example of FIG. 2, the implant 126 is a microcoil that deploys and at least partially fills the aneurysm 12.

When the operator (e.g., physician) determines that the implant 126 should be detached, one of the detachment mechanisms 105, 106 are activated. Again, the operator may select the detachment mechanism 105, 106 based on multiple factors or may default to a first detachment mechanism and then use the second detachment mechanism for backup purposes if the first detachment mechanism should fail. Alternatively, in some embodiments, the operator may select and activate both detachment mechanisms 105 and 106 simultaneously.

For example, the heater coil 108 is activated by pressing button 104A on the handle 104, causing electrical current to flow through the heater coil 108. As the heater coil 108 increases in temperature, it causes the tether 119 to break.

If, for some reason, the tether 119 does not break when the detachment mechanism 105 is actuated or activated, the detachment mechanism 106 can be actuated or activated. For example, the control wire 128 can be pulled from a proximal portion of the pusher 102 and/or handle 104. As the control wire 128 is pulled, it changes a position and/or angle of the tether 119 in the distal portion 102A of the pusher 102 so that the tether 119 moves against the blade edge 124 to cut or break the tether 119. Whether the first detachment mechanism 105 or the second detachment mechanism 106 breaks the tether 119, the implant 126 is ultimately detached and the delivery system 100 can be removed from the patient.

As previously discussed, other combinations of detachment mechanism are also possible.

For example, FIG. 5 illustrates another embodiment that is generally similar to the prior example but comprises a first detachment mechanism 130 with an electrolytic detachment mechanism and a similar mechanical second detachment mechanism 106. The first detachment mechanism 130 includes an electrolytically degradable portion 132 on the tether 119. In that respect, the tether may be electrically connected to one electrical wire 112 and another electrical wire/lead of the electrical circuit may be connected to the patient (e.g., via an electrical lead skin pad). Hence, when current is applied to the circuit, the electrolytic connection 132 may degrade and release the implant, though the second detachment mechanism 106 is also available should the first detachment mechanism 130 fail.

In another example, FIG. 6 illustrates another embodiment that is generally similar to the prior embodiments but comprises the detachment mechanisms 105, 106, and 130.

All three may be included, or any two may be included (e.g., only mechanism 105 and 130, or 106 and 130).

A tether 119 has been described in this specification. This term may also be considered a monofilament, thread, wire, or strand.

A heater or heater coil is described in this specification. This term may also be considered a heater tube, a heater loop, a heater wire, or any resistive element in any shape within a pusher that is capable of generating heat when supplied with electrical current.

A pusher is described in this specification. This term may also be considered any elongated body composed of any material, including polymer, metal, structural coils, electrical wires, or similar components. While the disclosed embodiments generally refer to the implant as being attached to the pusher, the implant could be attached to another component of the delivery device without changing the operation of the detachment mechanisms described herein. Within this context, other components of the delivery device may effectively act as a pusher as described in this specification.

While the present specification has generally discussed implant detachment systems with two or more detachment mechanisms, it is also contemplated that a single detachment system may also be included. For example, FIG. 7 illustrates a pusher 102 with only the mechanical, first detachment mechanism 105.

Additional uses and descriptions of the embodiments and examples described herein are provided below.

The delivery system for a medical implant may comprise: an elongated pusher; an implant positioned near a distal end of the elongated pusher; a first detachment mechanism configured to release the implant from the elongated pusher; and, a second detachment mechanism configured to release the implant from the elongated pusher.

The delivery system for a medical implant may comprise: an elongated pusher having a first detachment mechanism and a second detachment mechanism; and, an implant positioned near a distal end of the elongated pusher; wherein the implant has a detached state from the elongated pusher initiated by the second detachment mechanism when the first detachment mechanism fails to initiate the detached state.

A method of delivering a medical implant may comprise: advancing a distal end of a delivery system to a target area of a patient; actuating a first implant detachment mechanism within a pusher of the delivery system; and, actuating a second implant detachment mechanism within the pusher of the delivery system. The method may further comprise: wherein the actuating the first implant detachment mechanism comprises actuating or activating a heater. The method may further comprise: wherein the actuating the second implant detachment mechanism comprises actuating or activating a mechanical detachment system.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A delivery system for a medical implant, comprising:
an elongated pusher;
an implant positioned near a distal end of the elongated pusher;

a tether connected to the implant and the elongated pusher;
a first detachment mechanism having a first attached configuration where the implant is releasably secured to the elongated pusher, and having a first detached configuration where the implant is released from the elongated pusher; and,
a second detachment mechanism having a second attached configuration where the implant is releasably secured to the elongated pusher, and having a second detached configuration where the implant is released from the elongated pusher;
wherein the second detachment mechanism comprises a sharp edge or blade positioned or angled against the tether; and,
wherein the first detachment mechanism and the second detachment mechanism are both positioned on a proximal side of the implant.

2. The delivery system of claim 1, wherein initiation of the first detachment mechanism fails to release the implant from the pusher, the second detachment mechanism initiates release of the implant from the pusher.

3. The delivery system of claim 1, wherein either the first detachment mechanism or the second detachment mechanism may be first initiated to release the implant from the pusher.

4. The delivery system of claim 1, wherein the first detachment mechanism comprises a heater and a tether, and wherein the tether is connected to the implant and the elongated pusher.

5. The delivery system of claim 1, wherein the second detachment mechanism comprises a first position or angle of the tether within the elongated pusher in the second attached configuration, and a second position or angle of the tether within the elongated pusher in the second detached configuration wherein the tether is at least briefly positioned or angled against the sharp edge or blade to sever the tether.

6. The delivery system of claim 5, wherein the second detachment mechanism comprises a movable member having a first longitudinal position within the elongated pusher and a second longitudinal position within the elongated pusher.

7. The delivery system of claim 6, wherein the movable member further comprises a first passage within which the tether is positioned.

8. The delivery system of claim 7, wherein the movable member is attached to the elongated pusher via a track.

9. The delivery system of claim 8, further comprising a biasing element biasing the movable member in a non-detached position.

10. The delivery system of claim 7, further comprising a second passage positioned distally of the first passage and in which the tether is positioned within.

11. The delivery system of claim 10, wherein the second passage extends through a circular disc member.

12. The delivery system of claim 1, wherein the first detachment mechanism is one of a thermal detachment mechanism, electrolytic detachment mechanism, or a mechanical detachment mechanism.

13. The delivery system of claim 1, further comprising a sensor that determines whether the implant is attached to the pusher, and indicates to a user whether the implant is released from the pusher after activation of either the first or second detachment mechanism.

14. The delivery system of claim 13, further comprising an automatic activation mechanism, wherein if the sensor determines that the implant is attached to the pusher after activation of the first detachment mechanism, the automatic activation mechanism initiates the second detachment mechanism.

15. The delivery system of claim 13, wherein the sensor senses inductance at a distal portion of the pusher.

16. The delivery system of claim 1, wherein the first detachment mechanism and the second detachment mechanism are activated simultaneously.

17. A delivery system for a medical implant, comprising:
an elongated pusher;
an implant positioned near a distal end of the elongated pusher and releasably secured to the elongated pusher;
a tether connected to the implant and the elongated pusher;
a first detachment means to detach the implant from the elongated pusher; and,
a second detachment means to detach the implant from the elongated pusher, wherein the second detachment means comprises a sharp edge or blade positioned or angled against the tether; and,
wherein the first detachment means and the second detachment means are both positioned on a proximal side of the implant.

18. The delivery system of claim 17,
wherein the first detachment means comprises a thermal detachment mechanism,
and wherein one of the first detachment means or the second detachment means fully detaches the implant from the elongated pusher after the other detachment means fails to fully detach the implant from the elongated pusher.

19. A delivery system for a medical implant, comprising:
an implant positioned at a distal end of an elongated pusher,
a tether connected to the implant and the elongated pusher;
wherein the pusher has a first detachment mechanism and a second detachment mechanism,
wherein the second detachment mechanism comprises a sharp edge or blade positioned or angled against the tether,
wherein the implant is releasably attached to the pusher in an attached configuration prior to activation of the first detachment mechanism or if activation of the first detachment mechanism fails to release the implant from the pusher, and
wherein the implant is detached from the pusher in a detached configuration after activation of the first detachment mechanism or activation of the second detachment mechanism, or both; and,
wherein the first detachment mechanism and the second detachment mechanism are both positioned on a proximal side of the implant.

* * * * *